United States Patent
Morrison et al.

(10) Patent No.: US 8,043,853 B2
(45) Date of Patent: Oct. 25, 2011

(54) POSTNATAL GUT NEURAL CREST STEM CELLS

(75) Inventors: Sean J. Morrison, Ann Arbor, MI (US); Eve Kruger, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1254 days.

(21) Appl. No.: 10/640,914

(22) Filed: Aug. 14, 2003

(65) Prior Publication Data

US 2004/0110288 A1 Jun. 10, 2004

Related U.S. Application Data

(60) Provisional application No. 60/403,471, filed on Aug. 14, 2002.

(51) Int. Cl.
*C12N 5/00* (2006.01)
*C12N 5/079* (2010.01)
*C12N 5/0797* (2010.01)
*C12N 5/074* (2010.01)
*C12N 5/0735* (2010.01)

(52) U.S. Cl. .................. 435/368; 435/326; 435/366

(58) Field of Classification Search .................. None
See application file for complete search history.

(56) References Cited

U.S. PATENT DOCUMENTS 5,693,482 A * 12/1997 Anderson et al. ............... 435/29
5,928,947 A * 7/1999 Anderson et al. ............. 435/455
6,890,724 B2 * 5/2005 Anderson et al. ............ 435/7.21

OTHER PUBLICATIONS

Morshead. Dev. Neurosci. 2004. 26:93-100.*
Fuch et al. Cell 2000. 100: 143-155.*
Le Douarin et al. Curr. Opi. Genet. Dev 2003. 13: 529-536.*
Rietz et al.. Nature. 2001: 412: 736-739.*
LeDouarin, "Cell Line Segregation During Peripheral Nervous System Ontogeny," Science 231:1515 (1986).
Baroffio et al., "Common precursors for neural and mesectodermal derivatives in the cephalic neural crest," Development 112:301 (1991).
Reynolds and Weiss, "Generation of Neurons and Astrocytes from Isolated Cells of the Adult Mammalian Central nervous System," Science 255:1707 (1992).
Palmer et al., "The Adult Rat Hippocampus Contains Primordial Neural Stem Cells," Mol. Cell. Neurosci., 8:389 (1997).
Johansson et al., "Identification of a Neural Stem Cell in the Adult Mammalian Central Nervous System," Cell 96:25 (1999).
Doetsch et al., "Subventricular Zone Astrocytes Are Neural Stem Cells in the AdultMammalian Brain," Cell 97:703 (1999).
Altman, "Autoradiographic and Histological Studies of Postnatal Neurogenesis," J. Comp. Neurol., 137:433 (1969).
Eriksson et al., "Neurogenesis in the adult human hippocampus," Nature Medicine 4:1313 (1998).
Gould et al., "Neurogenesis in the Neocortex of Adult Primates," Science 286:548 (1999).
Rietze et al., "Purification of a pluripotent neural stem cell from the adult mouse brain," Nature 412:736 (2001).
Morrison et al., "Prospective Identification, Isolation by Flow Cytometry, and In Vivo Self-Renewal of Multipotent Mammalian Neural Crest Stem Cells," Cell 96:737 (1999).
Morrison et al., "Culture in Reduced Levels of Oxygen Promotes ClonogenicSympathoadrenal Differentiation by Isolated Neural Crest Stem Cells," J. Neurosci., 20:7370 (2000).
Pham et al., "Time of Origin of Neurons in the Murine Enteric Nervous Systems: Sequence in Relation to Phenotype," J. Comp. Neurol., 314:789 (1991).
Gershon et al., "Serotonergic neurons in the peripheral nervous system: Identification in gut by immunohistochemical localization of tryptophan hydroxylase," Proc. Natl. Acad. Sci. USA 74:3086 (1977).
Baetge et al., "Transiently Catecholaminergic (TC) Cells in the Bowel of the Fetal Rat: Precursors of Noncatecholaminergic Enteric Neurons," Dev. Biol. 141:353 (1990).

* cited by examiner

*Primary Examiner* — Chang-Yu Wang
(74) *Attorney, Agent, or Firm* — Casimir Jones, S.C.

(57) ABSTRACT

The present invention relates to compositions and methods employing postnatal (e.g., adult) neural crest stem cells. The stem cells are multipotent and differentiate when transplanted in vivo. Transplantation methods are provided for therapeutic, diagnostic, and research applications.

7 Claims, No Drawings

POSTNATAL GUT NEURAL CREST STEM CELLS

This invention claims priority to U.S. Provisional Patent Application No. 60/403,471, filed Aug. 14, 2002, the disclosure of which is herein incorporated by reference in its entirety.

This invention was made in part during work partially supported by the NIH Grant No. R01 NS40750-01. The government may have certain rights in the invention.

FIELD OF THE INVENTION

The present invention relates to compositions and methods employing postnatal (e.g., adult) neural crest stem cells.

BACKGROUND OF THE INVENTION

Recent published reports on the isolation and successful culturing of the first human pluripotent stem cell lines have generated great excitement and have brought biomedical research to the edge of a new frontier (National Institutes of Health, Office of the Director, "Stem Cells: A Primer"). Stem cells have the ability to divide for indefinite periods in culture and to give rise to specialized cells. They are best described in the context of normal human development. Human development begins when a sperm fertilizes an egg and creates a single cell that has the potential to form an entire organism. This fertilized egg is totipotent, meaning that its potential is total. In the first hours after fertilization, this cell divides into identical totipotent cells. This means that either one of these cells, if placed into a woman's uterus, has the potential to develop into a fetus. In fact, identical twins develop when two totipotent cells separate and develop into two individual, genetically identical human beings. Approximately four days after fertilization and after several cycles of cell division, these totipotent cells begin to specialize, forming a hollow sphere of cells, called a blastocyst. The blastocyst has an outer layer of cells and inside the hollow sphere, there is a cluster of cells called the inner cell mass.

The outer layer of cells will go on to form the placenta and other supporting tissues needed for fetal development in the uterus. The inner cell mass cells will go on to form virtually all of the tissues of the human body. Although the inner cell mass cells can form virtually every type of cell found in the human body, they cannot form an organism because they are unable to give rise to the placenta and supporting tissues necessary for development in the human uterus. These inner cell mass cells are pluripotent—they can give rise to many types of cells but not all types of cells necessary for fetal development. Because their potential is not total, they are not totipotent and they are not embryos. In fact, if an inner cell mass cell were placed into a woman's uterus, it would not develop into a fetus.

The pluripotent stem cells undergo further specialization into stem cells that are committed to give rise to cells that have a particular function. Examples of this include blood stem cells which give rise to red blood cells, white blood cells and platelets; and skin stem cells that give rise to the various types of skin cells. These more specialized stem cells are called multipotent.

While stem cells are extraordinarily important in early human development, multipotent stem cells are also found in children and adults. For example, consider one of the best understood stem cells, the blood stem cell. Blood stem cells reside in the bone marrow of every child and adult, and in fact, they can be found in very small numbers circulating in the blood stream. Blood stem cells perform the critical role of continually replenishing our supply of blood cells—red blood cells, white blood cells, and platelets—throughout life. A person cannot survive without blood stem cells.

Multipotent stem cells have not been found for all types of adult tissue, but discoveries in this area of research are increasing. For example, until recently, it was thought that stem cells were not present in the adult nervous system, but, in recent years, neural stem cells have been isolated from the rat and mouse nervous systems. The experience in humans is more limited. In humans, neural stem cells have been isolated from fetal tissue and a kind of cell that may be a neural stem cell has been isolated from adult brain tissue that was surgically removed for the treatment of epilepsy. In animals, it has been shown that some adult stem cells previously thought to be committed to the development of one line of specialized cells are able to develop into other types of specialized cells. For example, recent experiments in mice suggest that when neural stem cells were placed into the bone marrow, they appeared to produce a variety of blood cell types. In addition, studies with rats have indicated that stem cells found in the bone marrow were able to produce liver cells. These exciting findings suggest that even after a stem cell has begun to specialize, the stem cell may, under certain conditions, be more flexible than first thought.

Research on human adult stem cells suggests that these multipotent cells have great potential for use in both research and in the development of cell therapies. For example, there would be many advantages to using adult stem cells for transplantation. If one can isolate the adult stem cells from a patient, coax them to divide and direct their specialization and then transplant them back into the patient, it is unlikely that such cells would be rejected by the patient's immune system. The use of adult stem cells for such cell therapies could reduce the practice of using stem cells that were derived from human embryos or human fetal tissue, sources that trouble many people on ethical grounds.

While adult stem cells hold real promise, there are some significant limitations to what can be accomplished at present. Importantly, stem cells from adults have not been isolated for all tissues of the body. For example, researchers have not located adult cardiac stem cells or adult pancreatic islet stem cells in humans. Stem cells have never been found in the postnatal peripheral nervous system of any mammal. Additionally, adult stem cells are often present in only minute quantities, are difficult to isolate and purify, and their numbers may decrease with age. For example, available neural stem cells are obtained from adults only through very invasive procedures (e.g., brain biopsy).

Thus, what is needed are additional sources of stem cells to increase the ability to carry out cell transplantation therapies and additional methods of obtaining stem cells to allow reproducible and consistent acquisition of stem cells from tissues.

SUMMARY OF THE INVENTION

The present invention relates to compositions and methods employing neural crest stem cells. For example, the present invention provides compositions comprising a cell mixture, said mixture comprising isolated neural crest stem cells (e.g., p75 positive stem cells). The present invention also provides compositions comprising a cell mixture, said mixture comprising isolated postnatal neural stem cells. The present invention further provides a compositions comprising a cell mixture, said mixture comprising isolated neural stem cells isolated from the enteric nervous system or from the peripheral nervous system. The present invention also provides compositions comprising a cell mixture, said mixture comprising isolated postnatal neural crest stem cells isolated from the enteric nervous system. In some such embodiments, the stem cells are adult stem cells. The present invention is not limited by the source organism of the stem cells. In preferred embodiments, the source organism is mammal. In some preferred embodiments, the stem cells are isolated from the tissues of the gut.

In some embodiments, the composition comprises an in vitro cell culture. In some embodiments, the stem cells are self-renewable (e.g., in vitro or in vivo).

The stem cells of the present invention are multipotent. In preferred embodiments, the stem cells can be differentiated into neurons and/or glia.

The present invention also provides methods for using the stem cells. For example, the present invention provides a method for transplanting stem cells in vivo, comprising the steps of 1) providing: a host organism and isolated stem cells; and transplanting the stem cells into a tissue of the host. In some preferred embodiments, the stem cells are transplanted into an injured tissue of the host. In particularly preferred embodiments, the stem cells that are transplanted into the host are derived from the host (i.e., auto-transplantation). In some preferred embodiments, the stem cells comprise a transgene.

The present invention also provides methods for enriching a population of uncultured cells neural stem cells, comprising the steps of: a) providing uncultured cells from postnatal tissue, the tissue containing a neural stem cells; b) contacting the uncultured cells with a reagent that selectively binds to said neural stem cells (positive marker) or selectively binds cells other than neural stem cells (negative marker); and c) selecting cells that bind to the positive reagent or selecting cells that do not bind to the negative reagent, wherein selected cells are enriched in neural stem cells as compared with the uncultured cells. Cells can be selected using either positive or negative markers alone, or in combination. In preferred embodiments, the selected cells are enriched at least 20-fold (e.g., at least 100-fold) in neural stem cells as compared with said uncultured cells. In some preferred embodiments, the reagent is antibody. In some embodiments, the selecting step uses flow-cytometry. In yet other embodiments, the method further comprises the step of d) transplanting the selected cells into a host.

The present invention also provides a method for screening biological agents that affect proliferation, differentiation, gene expression, or survival of neural cells, comprising the steps of: 1) preparing a cell culture of neural stem cells; 2) contacting the stem cells with at least one test compound, and 3) determining if the test compound has an effect on proliferation, differentiation, gene expression, or survival of the stem cells (e.g., determining if the test compound enhances the ability of the stem cell to provide a therapeutic effect). The present invention is not limited by the nature of the test compound. In some embodiments, the test compound is a small molecule drug or a growth factor. In some embodiments, the screening method is carried out in vitro (e.g., in culture). In other embodiments, the screening method is carried out in vivo (e.g., in a host containing native or transplanted stem cells).

The present invention also provides methods for enhancing the ability of endogenous stem cells to provide therapeutic benefits to the surrounding tissue (e.g., injured tissue) comprising the step of administering to a host having stem cells an effective dose of a compound that promotes proliferation of differentiation of the stem cells, thereby therapeutically augmenting the ability of the stem cell to promote repair after injury. In some embodiments, the compound is a compound that directly or indirectly provides a growth factor to the stem cells (e.g., EGF, FGF).

Definitions

To facilitate an understanding of the present invention, a number of terms and phrases are defined below:

The term "transplant" refers to tissue used in grafting, implanting, or transplanting, as well as the transfer of tissues from one part of the body to another, or the transfer of tissues from one individual to another, or the introduction of biocompatible materials into or onto the body. The term "transplantation" refers to the grafting of tissues from one part of the body to another part, or to another individual.

As used herein, the term "stem cell" or "undifferentiated cell" refers to self-renewing multipotent cells that are capable of giving rise to more stem cells, as well as to various types of terminally differentiated cells.

As used herein, the term "host" refers to any warm blooded mammal, including, but not limited to, humans, non-human primates, rodents, and the like, which is to be the recipient of a particular treatment. Typically, the terms "host" and "patient" are used interchangeably herein in reference to a human subject.

As used herein, the terms "defective tissues" and "defective cells" refer to tissues and cells that are marked by subnormal structure, function, or behavior. Defects responsible for the defective tissues and cells include known or detectable defects, as well as, unknown or undetectable defects.

As used herein, the term "neural defect" refers to a defect involving or relating to the nervous system (including central and peripheral nervous systems). Some neural defects are caused by injury to the nervous system or defective tissues or cells of the nervous system, while other defects are caused by injury to cells that affect the nervous system or defective tissues or cells that affect the nervous system. As used herein, the term "neurally defective mammal" refers to a mammal having one or more neural defects. When a neural defect is "ameliorated," the condition of the host is improved. For example, amelioration can occur when defective tissue is returned partially or entirely to a normal state. However, amelioration can also occur when tissue remains subnormal, but is otherwise altered to benefit the host.

As used herein, the term "non-human animals" refers to all non-human animals. Such non-human animals include, but are not limited to, vertebrates such as rodents, non-human primates, ovines, bovines, ruminants, lagomorphs, porcines, caprines, equines, canines, felines, aves, etc.

The term "biologically active," as used herein, refers to a protein or other biologically active molecules (e.g., catalytic RNA) having structural, regulatory, or biochemical functions of a naturally occurring molecule.

The term "agonist," as used herein, refers to a molecule which, when interacting with a biologically active molecule, causes a change (e.g., enhancement) in the biologically active molecule, which modulates the activity of the biologically active molecule. Agonists may include proteins, nucleic acids, carbohydrates, small molecule drugs or any other molecules that bind or interact with biologically active molecules.

The terms "antagonist" or "inhibitor," as used herein, refer to a molecule which, when interacting with a biologically active molecule, blocks or reduces the biological activity of the biologically active molecule. Antagonists and inhibitors may include proteins, nucleic acids, carbohydrates, small molecule drugs or any other molecules that bind or interact with biologically active molecules. Inhibitors and antagonists can affect the biology of entire cells, organs, or organisms (e.g., an inhibitor that slows tumor growth).

The term "modulate," as used herein, refers to a change in the biological activity of a biologically active molecule. Modulation can be an increase or a decrease in activity, a change in binding characteristics, or any other change in the biological, functional, or immunological properties of biologically active molecules.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "isolated" when used in relation to a cell, as in "an isolated cell" or "isolated cells" refers to cells that are separated and enriched in a sample so as to remove the isolated cell(s) from other cells with which it is ordinarily associated in its natural environment. For example, isolated stem cells are stem cells that are removed from their natural environment and enriched in a sample, such that the sample housing the stem cells contains a higher percentage of stem cells than a corresponding sample found in a tissue in its natural environment.

The term "transgene" as used herein refers to a foreign gene that is placed into an organism or cell by, for example, transfection or introducing the foreign gene into newly fertilized eggs or early embryos. The term "foreign gene" refers to any nucleic acid (e.g., gene sequence) that is introduced into the genome of an animal or cell by experimental manipulations and may include gene sequences found in that animal so long as the introduced gene does not reside in the same location as does the naturally-occurring gene.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue (e.g., tissues of the gut or central nervous system), liquid foods (e.g., milk), and solid foods (e.g., vegetables).

GENERAL DESCRIPTION OF THE INVENTION

The present invention relates to compositions and methods employing postnatal (e.g., adult) neural stem cells. The inventors found neural crest stem cells (NCSCs) in the fetal and adult guts, and isolated them by flow-cytometry. The identification of NCSCs from the fetal and postnatal gut allowed a comparison their properties. Postnatal gut NCSCs self-renewed extensively in culture, although to a lesser extent than fetal gut NCSCs. Postnatal gut NCSCs made neurons that expressed a variety of neurotransmitters. Postnatal gut NCSCs also differed in their responsiveness to lineage determination factors relative to fetal gut NCSCs, affecting cell fate determination in vivo, and potentially explaining their reduced neuronal subtype potential. These perinatal changes in gut NCSCs parallel perinatal changes in the properties of hematopoietic stem cells, suggesting that stem cells in different tissues undergo similar developmental transitions. The persistence of NCSCs in the adult peripheral nervous system (PNS) opens up new routes for regeneration after injury or disease.

Most of the neurons and glia of the peripheral nervous system (PNS) arise during fetal development from the neural crest, a heterogeneous collection of progenitors that migrates out of the neural tube in mid-gestation (LeDouarin, Science 231:1515 (1986)). Migrating neural crest cells, which include neural crest stem cells (NCSCs), undergo progressive restrictions in developmental potential (Barofflo et al., Development 112:301 (1991)) and terminally differentiate soon after reaching postmigratory sites. The postnatal PNS was thought to lack stem cells.

Like the PNS, the adult CNS was once thought to lack stem cells. However, multipotent neural progenitors and neurogenesis do persist in certain regions of the adult CNS (Reynolds and Weiss, Science 255:1707 (1992), Palmer et al., Mol. Cell. Neurosci., 8:389 (1997), Johansson et al., Cell 96:25 (1999), Doetsch et al., Cell 97:703 (1999), Altman, J. Comp. Neurol., 137:433 (1969), Eriksson et al., Nature Medicine 4:1313 (1998), and Gould et al., Science 286:548 (1999)). Stem cells from the adult CNS have recently been prospectively identified and purified by flow-cytometry, creating the possibility of studying their properties as they exist in vivo (Rietze et al., Nature 412:736 (2001)).

Postmigratory rat NCSCs persist into late gestation by self-renewing within peripheral nerves and within the gut (Morrison et al., Cell 96:737 (1999)). At embryonic day 14.5 (E14.5), sciatic nerve NCSCs can be prospectively identified and isolated by flow-cytometry as $p75^+P_0^-$ cells, and gut NCSCs can be isolated as $p75^+\alpha_4^+$ cells. Seventy to eighty percent of single cells in each population self-renew and form multilineage colonies in culture that contain neurons, glia, and myofibroblasts (Morrison et al., 1999 and Morrison et al., J. Neurosci., 20:7370 (2000)). However, contrary to current beliefs about the existence of such cells, the present invention provides NCSCs that persist in the postnatal and adult gut and demonstrates that these cells undergo temporal changes in self-renewal potential, and neuronal subtype potential. Postnatal gut NCSCs gave rise to neurons and glia in vitro and in vivo.

DETAILED DESCRIPTION OF THE INVENTION

The present invention provides neural stem cells from postnatal gut tissue. The cells are shown to be multipotent. Methods are provided for obtaining such stem cells from mammals, including humans and for permitting self-renewal of the cells. Methods and compositions are provided for transplantation of the stem cells into organisms for therapeutic, diagnostic, and research uses.

For example, individual cells from the postnatal (P5-P22) and adult rat gut (P65-P110) formed large colonies in culture containing neurons, glia, and myofibroblasts, just as fetal NCSCs do. These multipotent progenitors were isolated by flow-cytometry as $p75^+$ cells and they self-renewed in culture confirming their identity as NCSCs. Uncultured P15 gut $p75^+$ cells gave rise to neurons and glia upon transplantation into the neural crest migration pathway of chick embryos. Thus, NCSCs, like CNS stem cells, persist in the adult nervous system. The persistence of NCSCs in the adult enteric nervous system (ENS) provides tissue for repair after gut injury, or transplantation from the gut to other sites of injury in the PNS.

Multipotent Neural Crest Progenitors Persist Throughout the Late Gestation PNS

Uncultured, postmigratory NCSCs can be isolated by flow-cytometry from freshly dissociated E14.5 rat sciatic nerve as cells that express the neurotrophin receptor, p75, but fail to express the peripheral myelin protein $P_0$ ($p75^+P_0^-$). More than eighty percent of $p75^+P_0^-$ cells are self-renewing, multipotent progenitors that give rise to neurons and glia in diverse regions of the embryonic chick peripheral nervous system (PNS). To test whether the sciatic nerve is unique in supporting the persistence of NCSCs into late gestation gut, dorsal root ganglia, and sympathetic ganglia from E14.5 rat fetuses was dissected. Each tissue was dissociated and cells were cultured at clonal density. Cells from each location gave rise to large multilineage colonies containing neurons, glia, and myofibroblasts. The overall appearance of these colonies was similar to that of migrating NCSCs derived from E10.5 neural tube explants or from postmigratory NCSCs obtained from E14.5 sciatic nerve (Morrison et al., 1999). These colonies also gave rise to many multipotent daughter cells when they were subcloned after 8 days in culture, demonstrating their self-renewal potential. This indicated that NCSCs persist in diverse regions of the mammalian PNS after migrating.

The Prospective Identification and Isolation of Gut NCSCs

The $P_0$ marker was not as effective in the gut as in the sciatic nerve at distinguishing stem cells from restricted progenitors. Therefore, additional markers were searched for that would allow the isolation of gut NCSCs. Using three-color flow-cytometry analysis, it was found that $p75^+P_0^-$ sciatic nerve NCSCs also expressed $\alpha_4$ integrin. In fact, a $p75^+\alpha_4^+$ population could be isolated from both the sciatic nerve and gut. Seventy-nine percent of sciatic nerve $p75^+\alpha_4^+$ cells gave rise to multilineage colonies in a clonal analysis, confirming that sciatic nerve NCSCs express $\alpha_4$ integrin. The $p75^+\alpha_4^+$ population from gut was also highly enriched for multipotent neural crest progenitors. Ten percent of unfractionated E14.5 gut cells survived to form colonies in culture and 11% of these cells formed multilineage colonies, indicating that around 1% of unfractionated gut cells are multipotent and survive in culture. All neural progenitor activity was contained within the $p75^+$ fraction of gut cells, as would be expected given that p75 consistently marks neural crest progenitors in the gut as well as in other locations. As p75 expression level increased, cells became increasingly enriched for the ability to form large multilineage colonies characteristic of NCSCs. In order to maximize the enrichment of multipotent progenitors and to include the majority of multipotent progenitors in the $p75^+\alpha_4^+$ population, the 1-2% of cells expressing the highest levels of p75 and $\alpha_4$ integrin by flow-cytometry were selected. In a clonal analysis, around 70% of these $p75^+\alpha_4^+$ cells formed multilineage colonies in culture.

The self-renewal potential of the $p75^+\alpha_4^+$ multipotent progenitors was measured by sorting individual cells into different wells of a 96-well plate, culturing for 8 days, and then subcloning individual colonies into secondary cultures to determine how many multipotent daughter cells were produced per multipotent founder cell. All 15 of the gut colonies that were subcloned gave rise to large numbers of multipotent daughter cells, as well as to various classes of restricted progenitors that were observed among freshly dissociated gut cells. The ability of single $p75^+\alpha_4^+$ gut cells to form multilineage colonies and to self-renew confirmed that they are NCSCs. Gut NCSCs gave rise to significantly more total subclones but significantly fewer glial-only subclones relative to sciatic nerve NCSCs.

Multipotent Progenitors Persist Postnatally in the Gut

The present invention provides multipotent progenitors from the postnatal gut and surrounding tissues. This discovery was originally found in rat gut. P5 to P15 rat gut was dissociated into single cell suspensions and plated in culture at clonal density. Clonal density allowed individual founder cells to form spatially distinct colonies so that the developmental potential of the founder cells could be assessed based on colony composition. After 14 days in culture the formation of multilineage colonies containing neurons, glia, and myofibroblasts that resembled colonies formed by embryonic NCSCs were consistently observed, though they tended to be somewhat smaller. Based on hemocytometer counts of trypsinized cells, multilineage colonies from E14.5 and P15 progenitors averaged 184,000±69,000 and 82,000±17000 cells per colony respectively.

To begin to assess the localization of these multipotent progenitors in vivo the plexus/outer muscle was stripped from the gut epithelium and these tissues were dissociated separately. It was found that multipotent progenitors were consistently cultured from the plexus/outer muscle layers, but never from the gut epithelium. This indicated that these multipotent progenitors were localized in vivo to the submucosal plexus, myenteric plexus, or outer muscle layers of the gut. All subsequent experiments on postnatal gut progenitors were performed using cells dissociated from the plexus/outer muscle layers.

Multipotent progenitors were infrequent among the unfractionated cells obtained from the preparations of dissociated P15 plexus/outer muscle layers. Only 0.7% of dissociated but unfractionated P15 cells survived and formed multilineage colonies in culture. Since p75 has consistently been observed to mark NCSCs in the gut and other tissues, tests were conducted to determine whether these multipotent progenitors were enriched within the $p75^+$ fraction of cells. As in the E14.5 gut, it was found that multipotent progenitors were enriched among cells with high levels of p75 expression. Although $p75^-$, and $p75^{low}$ cells formed no multilineage colonies and $p75^{med}$ cells gave rise to few multilineage colonies, $p75^+$ cells were highly enriched for multipotent progenitors. An average of fifty-two percent of $p75^+$ cells survived to form colonies in culture and 66% of these colonies were multilineage as shown in Table 1.

TABLE 1

Multipotent neural crest progenitors can be isolated as p75+ cells from the postnatal and adult gut

| | Plating Efficiency (%) | Colonies that contain the indicated cell types (%) | | | | | |
|---|---|---|---|---|---|---|---|
| | | N + G + M | N + M | N + G | G + M | G-only | M-only |
| E14.5 p75+α4+ | 45 ± 9 | 61 ± 21 | 3 ± 4 | 5 ± 5 | 11 ± 13 | 4 ± 4 | 15 ± 15 |
| P5 p75+ | 51 ± 9 | 65 ± 18 | 1 ± 1 | 14 ± 11 | 7 ± 7 | 6 ± 7 | 6 ± 4 |
| P10 p75+ | 44 ± 6 | 58 ± 25 | 0 ± 0 | 29 ± 35 | 6 ± 8 | 3 ± 3 | 4 ± 5 |
| P15 p75+ | 52 ± 12 | 66 ± 11 | 0 ± 0 | 12 ± 8 | 7 ± 5 | 11 ± 8 | 4 ± 5 |
| P22 p75+ | 50 ± 14 | 67 ± 18 | 0 ± 0 | 1 ± 2 | 13 ± 7 | 17 ± 7 | 1 ± 1 |
| P65-P110 p75+ | 9 ± 7 | 17 ± 23 | 0 ± 0 | 1 ± 1 | 22 ± 25 | 53 ± 28 | 7 ± 14 |

E14.5 gut p75+α4+ cells or postnatal gut p75+ cells were isolated by flow-cytometry and cultured at clonal density (40 cells/35 mm dish) for 14 days under standard conditions, then stained with antibodies against neurons (N; peripherin+), glia (G; GFAP+), and myofibroblasts (M; SMA+). Although postnatal gut cells were routinely stained for α4 integrin, the majority of p75+ cells were α4−, so use of the α4 marker did not increase NCSC enrichment. Therefore postnatal gut NCSCs were routinely isolated based only on their expression of high levels of p75. N+G+M colonies contained neurons, glia, and myofibroblasts, while M-only colonies contained only myofibroblasts. Each data point is shown as mean±standard deviation. Percentages do not necessarily add up to 100 because up to 2% of colonies did not stain with any marker. At P15 6±2% of unfractionated cells formed colonies and 13±4% of colonies were N+G+M. At P22 4±1% of unfractionated cells formed colonies and 5±4% of colonies were N+G+M. Interestingly, although E14.5 gut NCSCs are p75+α4+, p75+ cells were largely negative for α4 integrin by P15. By staining sections of P15 gut with an antibody against p75, it was found that p75+ cells localized to the myenteric and submucosal plexi.

Identification and Isolation of Postnatal Gut NCSCs by Flow-Cytometry

By isolating the 1-2% of cells that expressed the highest levels of p75 from the plexus/outer muscle layers of the gut it was found that highly enriched populations of NCSCs could be isolated from E14.5 through the oldest rat examined at P110 (Table 1). Sixty to seventy percent of colonies formed by p75+ cells from P5 to P22 gut contained neurons, glia, and myofibroblasts (N+G+M; Table 1). Additional colonies contained neurons and glia but not myofibroblasts (N+G). It is uncertain whether these N+G colonies represent restricted progenitors or whether some multipotent progenitors sometimes failed to make myofibroblasts under these culture conditions. Only 0.2% of unfractionated cells from the P22 plexus/outer muscle layer preparations survived and formed multilineage colonies in culture. Thus, taking into account plating efficiencies, multipotent progenitors were more than 150-fold enriched within the p75+ fraction of P22 gut cells relative to unfractionated cells.

Multipotent progenitors continued to be present within the adult (250 g rats; P65-110) rat gut. These multipotent progenitors were still highly enriched in the p75+ fraction of cells and largely negative for α4 integrin. However, the purity of multipotent progenitors among adult p75+ cells was much lower than in the P22 gut, with only 9% of cells surviving to form colonies in culture and 17% of colonies being multilineage.

Although neuron-only colonies were not detected from any of the postnatal gut p75+ cells after 14 days of culture, tests were conducted to be sure that this population was not substantially contaminated by committed neuronal progenitors or by immature neurons. To this end P15 p75+ cells were sorted into culture and the colonies were examined 4 days later. 2.3% of colonies contained a single neuron, and 0.6% of colonies contained two neurons. No neuron-only colonies contained more than 2 neurons. P15 p75+ cells were also sorted into culture and stained 17 hours later for the early neuronal marker neuron-specific (class III) β-tubulin (TuJ1 antibody). On average, 3.9±5% of P15 gut p75+ cells expressed β-tubulin. This suggests that around 4% of P15 p75+ cells are immature neurons or committed neuronal progenitors with the ability to divide once in culture.

Postnatal Gut Multipotent Neural Crest Progenitors Self-Renew in Culture

The self-renewal capacity of the gut multipotent progenitors was assayed by depositing single p75+ cells into individual wells of 96 well plates by flow-cytometry and then culturing for 8 days under standard conditions (Morrison et al. 1999). Multipotent colonies were then trypsinized and subcloned into secondary cultures at clonal density as previously described (Morrison et al., 1999). Almost all multipotent primary colonies gave rise to multipotent daughter colonies (20/20 at E14.5, 11/11 at P5, 16/18 at P15 and 6/6 at P22). Since the multipotent progenitors from postnatal gut were p75+, formed colonies similar to embryonic NCSC colonies, appeared to localize to the myenteric or submucosal plexi, and had the capacity to self-renew, it was concluded that they are postnatal NCSCs.

Although the postnatal gut NCSCs consistently self-renewed in culture, the extent of self-renewal quantitatively declined with increasing age. Each E14.5 gut NCSC produced an average of 730 multipotent daughter colonies (845 total daughter colonies) subclonable after 8 days in culture while P22 gut NCSCs produced an average of only 70 multipotent daughter colonies (360 total daughter colonies) under the same conditions (p=0.002; Table 2). NCSC self-renewal did not decline uniformly over time as some NCSCs at P15 and P22 self-renewed at a rate comparable to what was observed among E14.5 NCSCs. For example, one P15 NCSC gave rise to 370 multipotent daughter cells, while a P22 NCSC gave rise to 335 multipotent daughter cells.

TABLE 2

Postnatal gut NCSCs self-renew in culture with the extent of self-renewal declining with increasing age

| | | Subclones per multipotent founder cell | | | | |
|---|---|---|---|---|---|---|
| Population | Total | N + G + M | N + G | G + M | G-only | M-only |
| E14.5 gut p75$^+$α$_4$$^+$ | 845 a | 730 ± 459 a | 81 ± 151 | 27 ± 67 | 2 ± 5 a | 5 ± 10 |
| P5 gut p75$^+$ | 311 b | 146 ± 90 b | 15 ± 5 | 52 ± 23 | 96 ± 107 b | 2 ± 3 |
| P15 gut p75$^+$ | 386 b | 143 ± 143 b | 29 ± 50 | 69 ± 50 | 142 ± 100 b | 3 ± 7 |
| P22 gut p75$^+$ | 360 b | 70 ± 132 b | 22 ± 35 | 24 ± 31 | 242 ± 100 c | 2 ± 4 |
| Adult gut p75$^+$ | 366 | 35 ± 49 | 3 ± 3 | 110 ± 155 | 193 ± 230 | 24 ± 34 |

Secondary clones were cultured for 14 days and stained with antibodies to identify neurons (N), glia (G), and myofibroblasts (M) as described in Table 1. P22 gut NCSCs gave rise to significantly fewer total subclones and multipotent subclones but significantly more glial-only subclones than E14.5 NCSCs ($p < 0.05$). Significantly different statistics are followed by different letters, except for adult subclones which were not compared because they were subcloned after 15 days in culture.

The 8-15 day culture assay represents one way of quantitating self-renewal potential but it does not estimate the maximum self-renewal capacity of NCSCs. By culturing the postnatal gut NCSCs for longer periods of time they give rise to larger numbers of multipotent daughter cells.

NCSCs from the P15 Gut Differentiate into Neurons and Glia in vivo

To test the ability of the P15 gut NCSCs to generate neurons and glia in vivo, freshly-isolated, uncultured p75$^+$ cells were injected into 2 hindlimb bud somites of 8 stage 17-18 chick embryos. After 72 hours, embryos were fixed, sectioned, and processed for in situ hybridization using probes against rat SCG10 to identify neurons (Anderson and Axel, Cell 42:649 (1985)), and rat P0 to identify glia (Lemke et al., Neuron 1:73 (1988)). Chick neurons were identified by hybridizing with a chick SCG10 probe in some sections. Of 8 chicks analyzed, 4 showed engraftment with both neurons and glia, 2 showed engraftment of glia only, and 2 were not detectably engrafted. The failure of all 8 chicks to detectably engraft with both neurons and glia may be due to differences between postnatal gut NCSCs and embryonic gut NCSCs, or the relatively small numbers of cells injected (~310/somite; see Examples). Neuronal engraftment was found in sympathetic ganglia (2.2 cells/positive section) and glia were present in peripheral nerves (17.5 cells/positive section). Thus uncultured postnatal gut NCSCs migrated to embryonic neural crest structures and formed neurons and glia.

Postnatal Gut NCSCs Differentiate into Neurons that Express a Variety of Neurotransmitters A clonal analysis of gut NCSCs was performed to test whether they generate cells expressing a variety of neurotransmitters. NCSC colonies that had been cultured for 14 days at clonal density were stained using commercially available antibodies against vasoactive intestinal peptide (VIP), neuropeptide Y (NPY), and neuronal nitric oxide synthase (nNOS). Each of these antibodies specifically stained neurons based on analyses of adult rat gut sections and multilineage colonies in culture that were double labeled with these antibodies and antibodies against neuronal markers. VIP, NPY, and nitric oxide are all expressed by subsets of enteric neurons in vivo. Nearly all E14.5, P15, and adult gut NCSC colonies contained neurons expressing VIP, NPY, and nNOS. Based on these experiments, adult gut NCSCs retain the ability to generate neurons that express a variety of neurotransmitters normally found in the ENS.

Gut NCSCs Undergo Developmental Restrictions in Neuronal Subtype Potential

Neurons with different neurotransmitter phenotypes are born at different intervals of gut development (Pham et al., J. Comp. Neurol., 314:789 (1991)). Serotonergic progenitors last divide between E8 and E14.5 in mouse, while progenitors of NPY-expressing neurons last divide between E10 and P7. Since serotonergic differentiation is completed earliest during embryonic gut development, tests were conducted to examined whether gut NCSCs undergo restrictions between embryonic and postnatal stages in their potential to generate serotonergic neurons in culture.

Serotonergic neurons in the ENS can be identified by their expression of tryptophan hydroxylase, the initial and rate-limiting enzyme in the serotonin synthesis pathway (Gershon et al., Proc. Natl. Acad. Sci. USA 74:3086(1977)). E14.5 p75$^+$α$_4$$^+$ cells or P5 or p75$^+$ cells were cultured at clonal density for 14 days in standard medium and then stained with an antibody specific for tryptophan hydroxylase (Belin et al., Neuroscience Letters 125:101 (1991)). Tryptophan hydroxylase+neurons were present at low density in most multilineage colonies formed by E14.5 gut NCSCs (66±3%; FIGS. 6A, C), but only in few multilineage colonies formed by P5 gut NCSCs (9±5%; FIG. 6C). No P15 progenitors formed tryptophan hydroxylase±neurons in culture (0±0; FIGS. 6B, C). Between E14.5 and P15, NCSCs lost the ability to make serotonergic neurons based on this in vitro assay.

In addition to examining the ability of postnatal gut NCSCs to make subtypes of neurons that normally exist in the adult gut, experiments were conducted to examine their ability to make subtypes of neurons that differentiate only in other regions of the PNS. To this end, the ability of gut NCSCs to make noradrenergic neurons was examined. Although some gut neural crest progenitors transiently express a noradrenergic phenotype prior to E15 (tyrosine hydroxylase+ [TH+] and dopamine-B-hydroxylase+ [DBH+]), these cells continue to proliferate and TH can no longer be detected in the gut after E15 (Baetge et al., Dev. Biol. 141:353 (1990)).

NCSCs were isolated from rats ranging in age from E14.5 to P22 and cultured under conditions that promote noradrenergic differentiation (Morrison et al., 2000a). These cultures were double-labeled with antibodies against peripherin (to identify neurons) and either tyrosine hydroxylase (TH) or dopamine-β-hydroxylase (DPH). All TH$^+$ or DβH$^+$ cells co-expressed peripherin, but only a minority of peripherin positive neurons expressed TH or DβH. Double labeling experiments with antibodies against TH and DβH demonstrated that all of the TH$^+$ cells examined co-expressed DβH, but DβH$^+$ cells often did not express TH. The percentage of DβH positive cells also expressing TH declined with age. At E14.5 an average of 51.7±14.5% of DβH positive cells also expressed TH but at P15 only 23.4±21.4% of DβH$^+$ cells did (p<0.05). This is consistent with the fact that gut neural crest progenitors can give rise to both noradrenergic neurons (TH$^+$DβH$^+$) as well as DβH$^+$TH$^-$ neurons that are peptidergic but not catecholaminergic (Baetge et al., 1990).

Nearly all E14.5 gut NCSC colonies contained neurons that expressed TH (87±3%) and/or DβH (85±12%) but the percentage of gut NCSCs that formed such neurons declined with increasing stem cell age as shown in Table 3. By P15, only 20% of NCSCs formed TH$^+$ neurons and 38% formed DβH$^+$ neurons (both differences were statistically significant; p<0.01). In addition to the reduction in the proportion of NCSCs that were able to form such cells, there was also a reduction in the number of such cells per colony. While E14.5 gut NCSC colonies contained an average of 444±285 DβH$^+$ cells and 307±244 TH$^+$ cells, P15 gut NCSC colonies averaged only 14±13 DβH$^+$ cells and 2±1 TH$^+$ cells. This reduction in the number of noradrenegic neurons per colony cannot be explained by a proportionate decline in the total number of neurons per colony as we estimated that E14.5 gut NCSC colonies averaged 41,000±25,000 neurons/colony while P15 gut NCSCs averaged 16,000±13,000 neurons per colony. Thus the frequency of noradrenergic neurons declined much more precipitously that the total neurons per colony over this developmental interval.

Enteric neural crest progenitors have been observed to transiently express TH and DβH, in early embryonic development (before E15) prior to differentiating. To be certain that these NCSC cultures did not contain proliferating TH or DβH positive progenitors, BrdU was added for the final 24 hours of culture prior to immunohistochemical staining. Consistent with their neuronal morphology, double labeling experiments with TH and BrdU indicated that the vast majority of TH$^+$ cells were not proliferative: while 22% of all cells in colonies containing TH$^+$ cells were BrdU$^+$, only 1.9% of the cells expressing TH had incorporated BrdU.

Postnatal Gut NCSCs are More Responsive to Gliogenic Factors than Embryonic Gut NCSCs Based on an analysis of rats that were administered BrdU from P14-16, many more newborn glial cells were detected than neurons in the gut during this period. Experiments showed that postnatal gut NCSCs became increasingly responsive to the gliogenic effects of soluble Notch ligand, Delta-Fc, with increasing time after birth. Although few or no glial-only colonies were detected from E14.5 gut NCSCs treated with soluble Delta, P5 and P15 gut NCSCs did generate significantly increased numbers of glial-only colonies after treatment with soluble Delta. Treatment with soluble Delta increased the formation of glial-only colonies by P15 NCSCs by over 40% while increasing plating efficiency by only 10-13%. Postnatal gut NCSCs become responsive to the gliogenic effect of Notch activation in a way that is not observed among E14.5 gut NCSCs. P15 gut NCSCs are also more responsive to the gliogenic effects of Neuregulin than E14 gut NCSCs.

Temporal Changes in the Responsiveness of Gut NCSCs to Lineage Determination Factors Affect Cell Fate Determination in vivo P15 gut NCSCs are less responsive to the neurogenic factor BMP4 but are more responsive to gliogenic factors than E14.5 gut NCSCs. If temporal changes in the responsiveness of gut NCSCs to lineage determination factors affect cell-fate determination in vivo, then P15 gut NCSCs should give rise primarily to glia upon transplantation into developing chick nerves, in contrast to E14.5 gut NCSCs, which gave rise primarily to neurons. To test this the peripheral nerves of chicks injected with uncultured P15 gut NCSCs were examined. Six of 8 chicks exhibited glia in their peripheral nerves (17.5 cells/positive section) while 1 of 8 chicks had a single neuron in a peripheral nerve. Thus P15 gut NCSCs are biased toward adopting a glial fate in developing peripheral nerves, like E14.5 sciatic nerve NCSCs but unlike E14.5 gut NCSCs. This demonstrates that NCSCs undergo perinatal changes in their responsiveness to lineage determination factors that affect cell fate determination in vivo.

Transplantation

As described above, the neural crest stem cells of the present invention are able to be transplanted in vivo and to differentiate. Thus, the stem cells of the present invention provide compositions that find use in therapeutic, diagnostic and research applications.

Therapeutic applications include the transplantation of neural stem cells to injured and diseased tissue. In some preferred embodiments, cells from a particular host are used to transplant into a different region of the host. Such autotransplanation minimizes concerns about adverse immune responses. Use of cells from the gut also provides a much less invasive procedure than obtaining cells from brain biopsies. Thus, in some embodiments, a host with an injury has stem cells taken from gut and transplanted to the site of injury. As with other transplantation techniques, the present invention also provides methods for allotransplantation of cells (e.g., between a donor sibling and a recipient sibling; between an immunologically matched or partially matched donor and recipient, etc.).

In some such embodiments, the cells differentiate and provide replacements or surrogates for cells lost to injury. For example, the stem cells occupy the region of the injury to take over the function of lost or damaged cells or are used to secrete proteins or other factors needed in the damaged or diseased tissue. Differentiation can occur in vivo or in vitro. Indeed, the present invention is not limited by the manner in which the transplantation occurs. For example, in some embodiments, stem cells are cultured and expanded in vitro prior to transplantation. In some embodiments, the stem cells are differentiated or predifferentiated in culture prior to transplantation. Such methods find particular use where a desired cell type or fate is desired at the site of transplantation.

In some such embodiments, the neural crest stem cells express a transgene. For example, transgenes include native genes that are overexpressed to generate large amounts of a desired factor (e.g., a secreted protein or peptide), therapeutic genes, or any other desired factor (See e.g., Park et al., Gene Ther. 9:613 (2002)).

The term "genetic modification" as used herein refers to the stable or transient alteration of the genotype of a precursor cell by intentional introduction of exogenous nucleic acid. Nucleic acid may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like.

Exogenous DNA may be introduced to a stem cell by viral vectors (retrovirus, modified herpes viral, herpes-viral, adenovirus, adeno-associated virus, and the like), direct DNA transfection (lipofection, calcium phosphate transfection, DEAE-dextran, electroporation, and the like), or any other suitable method.

In another embodiment, the stem cells are derived from transgenic animals, and thus are in a sense already genetically modified. There are several methods presently used for generating transgenic animals. The technique used most often is direct microinjection of DNA into single-celled fertilized eggs. Other techniques include retroviral-mediated transfer, or gene transfer in embryonic stem cells. Use of these transgenic animals has certain advantages including the fact that there is no need to transfect healthy cells. Stem cells derived from transgenic animals will exhibit stable gene expression. Using transgenic animals, it is possible to breed in new genetic combinations. The transgenic animal may have integrated into its genome any useful gene that is expressed by neural cells.

When the genetic modification is for the production of a biologically active substance, the substance will generally be one that is useful for the treatment of a given disorder. For example, it may be desired to genetically modify cells so they secrete a certain growth factor product. As used herein, the term "growth factor product" refers to a protein, peptide, mitogen, or other molecule having a growth, proliferative, differentiative, or trophic effect. Growth factor products useful in the treatment of nervous system disorders include, but are not limited to, NGF, BDNF, the neurotrophins (NT-3, NT-4/NT-5), CNTF, amphiregulin, FGF-1, FGF-2, EGF, TGFα, TGFβs, PDGF, IGFs, and the interleukins.

Cells can also be modified to express a certain growth factor receptor (r) including, but not limited to, p75 low affinity NGFr, CNTFr, the trk family of neurotrophin receptors (trk, trkB, trkc), EGFr, FGFr, and amphiregulin receptors. Cells can be engineered to produce various neurotransmitters or their receptors such as serotonin, L-dopa, dopamine, norepinephrine, epinephrine, tachykinin, substance-P, endorphin, enkephalin, histamine, N-methyl D-aspartate, glycine, glutamate, GABA, ACh, and the like. Useful neurotransmitter-synthesizing genes include TH, DDC, DBH, PNMT, GAD, tryptophan hydroxylase, ChAT, and histidine decarboxylase. Genes that encode for various neuropeptides, which may prove useful in the treatment of nervous system disorders, include substance-P, neuropeptide-Y, enkephalin, vasopressin, VIP, glucagon, bombesin, CCK, somatostatin, calcitonin gene-related peptide, and the like.

Any suitable transplantation technique may be used. For example, methods for transplanting cells to specific regions of the central nervous system are taught by U.S. Pat. No. 5,650,148, incorporated herein by reference. Methods for transplanting various nerve tissues have been described in Neural Grafting in the Mammalian CNS, (Bjorklund and Stenveni, eds. [1985]); Das, Ch. 3 pp. 23-30; Freed Ch. 4, pp. 31-40; Stenevi et al., Ch. 5, pp. 41-50; Brundin et al., Ch. 6, pp. 51-60; David et al., Ch. 7, pp. 61-70; and Seiger, Ch. 8, pp. 71-77), herein incorporated by reference. In some grafting embodiments, a cell suspension is drawn up into a syringe and administered to anesthetized graft recipients. Multiple injections may be made using this procedure. The use of such cellular suspension procedures provides many advantages. For example, these methods permit grafting cells to any predetermined site, are relatively non-traumatic, allow multiple grafting simultaneously in several different sites or the same site using the same cell suspension, and permit the use of mixed cells obtained from different anatomical regions. Preferably, from approximately $10^4$ to approximately $10^8$ cells are introduced per graft, although certain applications may require higher or lower numbers.

Typically, the number of cells transplanted into the patient or host will be a "therapeutically effective amount." As used herein, "therapeutically effective amount" refers to the number of transplanted cells that are required to effect treatment of the particular disorder for which treatment is sought. For example, where the treatment is for tissue injury, transplantation of therapeutically effective amount of cells will typically produce a reduction in the amount and/or severity of the symptoms associated with the injury. Persons of skill in the art will understand how to determine proper cell dosages.

In some embodiments, it may be desired that the stem cells be treated prior to transplantation in order to reduce the risk of stimulating host immunological response against the transplanted cells. For example, in some embodiments, the cells are encapsulated by membranes prior to implantation. The encapsulation provides a barrier to the host's immune system and inhibits graft rejection and inflammation. It is contemplated that any of the many methods of cell encapsulation available will be employed. In some instances, cells are individually encapsulated. In other instances, many cells are encapsulated within the same membrane. In embodiments in which the cells are removed following implantation, the relatively large size of a structure encapsulating many cells within a single membrane provides a convenient means for retrieval of the implanted cells. Several methods of cell encapsulation are well known in the art, such as those described in European Patent Publication No. 301,777 or U.S. Pat. Nos. 4,353,888; 4,744,933; 4,749,620; 4,814,274; 5,084,350; 5,089,272; 5,578,442; 5,639,275; and 5,676,943, each of which is incorporated herein by reference.

Neural stem cell progeny when administered to the particular neural region preferably form a neural graft, wherein the neuronal cells form normal neuronal or synaptic connections with neighboring neurons, and maintain contact with transplanted or existing glial cells which may form myelin sheaths around the neurons' axons, and provide a trophic influence for the neurons. As these transplanted cells form connections, they re-establish the neuronal networks that have been damaged due to disease, injury, and aging.

In other embodiments, stem cells that have differentiated or are to differentiate into glia are transplanted to a desired site in the host. Such embodiments find use, for example, in the treatment and/or prevention of demyelenating diseases and disorders.

As desired, neural stem cells and their progeny can be induced to proliferate and differentiate in vivo by administering to the host, any growth factor(s) or pharmaceutical composition that will induce proliferation and differentiation of the cells. These growth factors include any growth factor known in the art, including the growth factors described above for in vitro proliferation and differentiation. Pharmaceutical compositions include any substance that blocks the inhibitory influence and/or stimulates neural stem cells and stem cell progeny to proliferate and ultimately differentiate. In some embodiments, drugs or other compounds are provided to the host to enhance a desired property of the stem cells. Indeed, the stem cells of the present invention provide methods for screening, identifying, and selecting such factors in vivo or in vitro, whereby a test compound is exposed to the cells and presence or absence of a desired activity is detected. By therapeutically enhancing the ability of the endogenous cells to repair injuries, it may be possible to avoid the need for transplantation of exogenous stem cells.

In some embodiments, transplanted cells are used for diagnostic and/or research purposed. For example, in some embodiments, cells are transplanted into a host and the host is exposed to stimuli (e.g., drugs, diets, aging, hormones, etc.) so that the effect of the stimuli on differentiation of the stem cell can be monitored. In some embodiments, the transplanted cells comprise a transgene that, upon expression, provides a marker. The marker may be used to identify the cells in the host or to identify an effect on the transplanted cells caused by their environment.

EXPERIMENTAL

The following examples are provided in order to demonstrate and further illustrate certain preferred embodiments and aspects of the present invention and are not to be construed as limiting the scope thereof.

Example 1

Isolation of Postnatal Gut Cells

Sprague-Dawley rats were obtained from Simonsen (Gilroy, Calif.). The small intestine was separated from attached mesentery and placed in cold Ca,Mg-free HBSS (Gibco, Grand Island N.Y.). Outer muscle/plexus layers were peeled free of the underlying epithelium as previously described (Schafer et al., Brain Research Protocols 1:109 (1997)), minced, and dissociated in 0.025% trypsin/EDTA (Gibco product 25300-054) plus 1 mg/ml type 4 collagenase (Worthington, Lakewood N.J.) in Ca, Mg-free HBSS for 8 minutes at 37° C. Adult gut was dissociated for 20 minutes in the same enzymes. The digestion was quenched with 2 volumes of staining medium: L15 medium containing 1 mg/mL BSA (Sigma product A-3912, St. Louis Mo.), 10 mM HEPES (pH 7.4), penicillin/streptomycin (BioWhittaker), and 25 µg/mL deoxyribonuclease type 1 (Sigma, product D-4527). After centrifuging, gut cells were triturated, filtered through a nylon screen (45 µm, Sefar America, Kansas City Mo.) to remove aggregates of cells and undigested tissue, and resuspended in staining medium. E14.5 gut, including stomach, small intestine, and hindgut were dissected from the same embryos and dissociated by incubating for 2 minutes at 37° C. in 0.5mg/ml deoxyribonuclease type 1 (Sigma) in Ca, Mg-free HBSS.

Example 2

Flow-cytometric Isolation of NCSCs and Cell-cycle Analysis

Flow cytometric isolation of gut NCSCs was performed on a FACSVantage dual-laser flow-cytometer (Becton-Dickinson, San Jose). Gut cells were stained with antibodies against p75 and α4 integrin (Becton Dickinson, MRα4-1 clone, directly conjugated to phycoerythrin). After washing off unbound antibodies, cells were resuspended in staining medium containing 2 µg/ml 7-AAD (Molecular Probes, Eugene Oreg.). Dead cells were eliminated from sorts and analyses as 7-AAD$^+$. Sciatic nerve NCSCs were isolated as p75$^+$P$_0^-$ and gut NCSCs were isolated as p75$^+$α$_4^+$. When sorting into culture, great care was taken to maintain a physiological pH in the culture medium by keeping the plates sealed in plastic bags containing 6% $CO_2$ before and after sorting.

For cell cycle analyses using Hoechst 33342, dissociated gut cells were suspended at a concentration of 1-2×10$^6$ cells /ml in staining medium containing 4 µg/ml Hoechst 33342 (Sigma) and 50 µg/ml verapamil (Sigma) to block MDR-mediated Hoechst efflux. Cells were incubated for 45 minutes at 37° C. and agitated every 5-10 minutes to prevent settling. Immediately after incubation the cells were put on ice and stained with antibodies as described above. Hoechst staining of NCSCs was assayed by flow-cytometry.

Example 3

Cell Culture

Cells were typically cultured in 6-well plates (Corning, Corning N.Y.) at clonal density so that individual colonies were spatially distinct (fewer than 30 clones per well for 14 day cultures) as previously described (Morrison et al., 1999, Morrison et al., 2000). Plates were sequentially coated with 150 µg/ml poly-d-lysine (Biomedical Technologies, Stoughton Mass.) and 0.15 mg/mL human fibronectin (Biomedical Technologies) as described (Stemple and Anderson, Cell 71:973 (1992)). The culture medium contained DMEM-low (Gibco, product 11885-084) with 15% chick embryo extract (prepared as described (Stemple and Anderson, 1992), 20 ng/mL recombinant human bFGF (R&D Systems, Minneapolis), 1% N2 supplement (Gibco), 2% B27 supplement (Gibco), 50 µM 2-mercaptoethanol, 35 mg/mL (110 nM) retinoic acid (Sigma), penicillin/streptomycin (Biowhittaker), and 20 ng/ml IGF1 (R&D Systems). IGF1 promotes the survival of neural crest progenitors without influencing their differentiation. This medium composition is described as 'standard medium'. Under standard conditions, cells were cultured for 6 days in this medium, then switched to a similar medium (with 1% CEE and 10 ng/mL bFGF) that favors differentiation for another 8 days before immunohistochemical analysis of colony composition. All cultures were maintained in gas-tight chambers (Billups-Rothenberg, Del Mar, Calif.) containing decreased oxygen levels as previously described to enhance the survival of NCSCs (Morrison et al., 2000). Delta-Fc or Fc were added to some cultures as previously described (Morrison et al., Cell 101:499 (2000)).

To promote the differentiation of noradrenergic neurons, NCSCs were cultured in standard medium for 6 days, followed by 6 days in differentiation medium supplemented with 5 µM forskolin (Sigma) and 1 ng/ml BMP4 (R&D Systems), followed by a final 6 days in differentiation medium supplemented with 50 ng/ml nerve growth factor and neurotrophin-3 as previously described (Morrison et al., 2000).

Example 4

BrdU Labeling In Vivo

The mitotic activity of postnatal gut NCSCs in vivo was assayed by administering 5'-bromo-2'-deoxyuridine (BrdU, Sigma) to rat pups for 20 hours prior to dissecting guts at P15. Doses of BrdU equivalent to 50 µg/g body weight were dissolved in 1 mL D-PBS with 0.007 M NaOH and injected intraperitoneally at 20, 16, and 2 hours before dissection. In one experiment additional injections were performed 18 and 14 hours before dissection. NCSCs were isolated from the BrdU administered or control rats, allowed to adhere to tissue culture plates for 18 hours, and stained with an antibody against BrdU (Caltag product IU-4, Burlingame Calif.) (Raff et al., Nature 333:562 (1988)).

Example 5

Immunocytochemistry

Cultures were fixed in acid ethanol (5% glacial acetic acid in 100% ethanol) for 20 minutes at −20° C., washed, blocked and triply labeled for peripherin (Chemicon AB1530; Temecula Calif.), GFAP (Sigma G-3893) and alpha SMA (Sigma A-2547) as described (Shah et al., Cell 85:331 (1996)). MASH-1 staining was performed as described (Shah et al., Cell 77:349 (1994)). Plates stained for neuronal subtype markers were fixed in fresh 4% paraformaldehyde for 10 minutes at room temperature, washed and blocked as described (Shah et al., 1994). Antibodies were obtained as follows: tyrosine hydroxylase (TH) (Chemicon, product #MAB5280), dopamine-B-hydroxylase (DBH; BD PharMingen, #556313), neuropeptide Y (NPY; Peninsula Laboratories, #IHC 7161, San Carlos, Calif.), vasoactive intestinal peptide (VIP; Peninsula Laboratories, #IHC 7180), neuronal nitric oxide synthase (nNOS; Chemicon, #AB5380), and tryptophan hydroxylase (Chemicon, #AB1541). In some experiments, plates were co-labeled with NeuN (Chemicon, #MAB377) to confirm that neuronal subtype antibodies were labeling neurons. For p75 (Promega prod. 1405-41-0) staining of gut sections, tissue was fixed in freshly prepared 4% paraformaldehyde and embedded in paraffin.

Example 6

In Vivo Transplantation of Neural Crest Progenitors

Fertile White Leghorn eggs (Bilbie Aviaries, Ann Arbor, Mich.) were incubated to Hamburger and Hamilton stage 17-18 (Hamburger and Hamilton, J. Morphology 88:49 (1951)) and injected with P15 gut p75$^+$ cells. Approximately 70,000 p75$^+$ cells were isolated by flow-cytometry, back-loaded into a drawn glass capillary tube (World Precision Instruments, Sarasota Fla.), centrifuged for 2 min at 52×g, and injected into the anterior, medial corner of two somites in the himblimb bud region of each embryo. Injections were performed using a Narishige H-7 pipette holder mounted on a MM-33 micromanipulator (Fine Science Tools, Forester City, Calif.) and very gentle air pressure. The number of cells injected per somite was estimated as 310±20 cells by labeling sorted P15 p75$^+$ cells with DiI, and then counting the number of DiI+ cells/somite immediately after injection. Injected embryos were incubated for 3 days, to stage 29, fixed, embedded in OCT and cryostat sectioned. To control for nonspecific hybridization, sections from E16.5 rat and uninjected stage 29 chicks were processed in parallel as positive and negative controls, and sections adjacent to those showing engraftment were probed with the sense strands of SCG10 and P$_0$. Since embryos were unilaterally injected, the contralateral side to engraftment also served as a negative control.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising a cell mixture, said mixture comprising isolated postnatal gut neural crest stem cells, wherein said isolated postnatal gut neural crest stem cells are P15 to adult postnatal gut neural crest stem cells, wherein said P15 to adult postnatal gut neural crest stem cells do not make serotonergic neurons.

2. The composition of claim 1, wherein said postnatal gut neural crest stem cells comprise adult gut neural crest stem cells.

3. The composition of claim 1, wherein said postnatal gut neural crest stem cells comprise p75-positive postnatal gut neural crest stem cells.

4. The composition of claim 1, wherein said composition comprises an in vitro cell culture.

5. The composition of claim 1, wherein said postnatal gut neural crest stem cells are self-renewable.

6. The composition of claim 1, wherein said postnatal gut neural crest stem cells can be differentiated into neurons.

7. The composition of claim 1, wherein said postnatal gut neural crest stem cells can be differentiated into glia.

* * * * *